(12) United States Patent
Furuta

(10) Patent No.: US 7,696,376 B2
(45) Date of Patent: Apr. 13, 2010

(54) METHOD FOR MANUFACTURE OF ESTERS BY TRANSESTERIFICATION

(75) Inventor: Satoshi Furuta, Toda (JP)

(73) Assignee: Japan Energy Corporation, Minato-ku, Tokyo (JP)

( * ) Notice: Subject to any disclaimer, the term of this patent is extended or adjusted under 35 U.S.C. 154(b) by 149 days.

(21) Appl. No.: 10/558,935

(22) PCT Filed: Jun. 23, 2004

(86) PCT No.: PCT/JP2004/009250

§ 371 (c)(1),
(2), (4) Date: Dec. 1, 2005

(87) PCT Pub. No.: WO2005/000782

PCT Pub. Date: Jan. 6, 2005

(65) Prior Publication Data

US 2007/0027338 A1     Feb. 1, 2007

(30) Foreign Application Priority Data

Jun. 30, 2003  (JP) .............................. 2003-186045
Nov. 20, 2003  (JP) .............................. 2003-390092

(51) Int. Cl.
*C07C 67/02* (2006.01)
(52) U.S. Cl. ........................ 560/234; 560/217; 554/174
(58) Field of Classification Search ................. 560/217, 560/234; 554/174
See application file for complete search history.

(56) References Cited

U.S. PATENT DOCUMENTS 5,508,457 A * 4/1996 Bayense et al. ............. 554/169
6,090,959 A    7/2000 Hirano et al.
6,166,170 A * 12/2000 Putzig ........................ 528/279
6,255,441 B1 * 7/2001 Putzig et al. ................ 528/271
6,887,283 B1 * 5/2005 Ginosar et al. ................ 44/388

FOREIGN PATENT DOCUMENTS

| EP | 1 505 048 A1 | 2/2005 |
|----|----|----|
| JP | 6-313188 | 11/1994 |
| JP | 7-173103 | 7/1995 |
| JP | 7-197047 | 8/1995 |
| JP | 9-235573 | 9/1997 |
| JP | 2000-143586 | 5/2000 |
| JP | 2001-17862 | 1/2001 |
| JP | 2001-253714 | 9/2001 |

OTHER PUBLICATIONS

Pradeep Kumar, Rajesh Kumar Pandey. A facile and selective procedure for transesterification of b-keto esters promoted by yttria-zirconia based Lewis acid catalyst. Synlett, 251-253, 2, 2000.*

* cited by examiner

*Primary Examiner*—Daniel M Sullivan
*Assistant Examiner*—Sudhakar Katakam
(74) *Attorney, Agent, or Firm*—Flynn, Thiel, Boutell & Tanis, P.C.

(57) ABSTRACT

A method for the manufacture of an ester by transesterification allows the transesterification reaction to proceed within a short reaction time and under a pressure of the order of normal pressure. It was found that transesterification proceeds when a starting material ester and an alcohol are brought into contact with a catalyst comprising (A) an amorphous zirconium oxide and (B) an oxide of a Group II element, an oxide of a Group V element, and/or an oxide of a Group IV element other than zirconium and hafnium. In this method, it is preferred that the starting material ester in a liquid-phase state and the alcohol in a vapor-phase state be brought into contact with a solid acid catalyst comprising the above components (A) and (B), the starting material ester be an oil or fat, and the alcohol be methanol or ethanol. An oxide of titanium, silicon, germanium, or tin is the preferred oxide of the Group IV element other than zirconium and hafnium.

9 Claims, No Drawings

METHOD FOR MANUFACTURE OF ESTERS BY TRANSESTERIFICATION

The present application is a national stage application of PCT/JP04/09250, filed under 35 USC 371.

TECHNICAL FIELD

The present invention relates to a method for the manufacture of esters such as fatty acid esters from starting material esters such as triglycerides, diglycerides, and monoglycerides by transesterification.

BACKGROUND ART

Transesterification is used for the manufacture of fatty acid esters, for example, by using oils and fats which are esters of fatty acids and glycerin. Alkali catalysts such as caustic soda, zinc catalysts, and lipase can be used as catalysts. Furthermore, it was also suggested to conduct the reaction in a supercritical state, without the addition of a catalyst (Japanese Patent Publication Nos. 9-235573A, 7-197047A, and 2000-143586A).

DISCLOSURE OF THE INVENTION

When an alkali catalyst such as caustic soda is used, the reaction time is long and the catalyst has to be separated after the reaction. Furthermore, when the starting materials contain a large quantity of free fatty acids, pretreatment is required to remove them. Another problem was that transesterification could not proceed due to a saponification reaction. When a zinc catalyst was used or when the reaction proceeded in a supercritical state, the reaction typically had to be conducted under a pressure as high as 5 MPa to 8 MPa.

It is an object of the present invention to provide a method for the manufacture of esters by transesterification, this method allowing the transesterification to proceed within a short reaction time and under a pressure of the order of normal pressure.

The inventors have found that transesterification is promoted if a starting material ester and an alcohol are brought into contact with a catalyst comprising (A) an amorphous zirconium oxide and (B) an oxide of Group III element, an oxide of Group V element, and/or an oxide of Group IV element other than zirconium and hafnium. In this method, it is preferred that a starting material ester in a liquid-phase state and an alcohol in a vapor-phase state be brought into contact with a solid acid catalyst comprising the above components (A) and (B), the starting material ester be an oil or fat, and the alcohol be methanol or ethanol. The content of amorphous zirconium oxide as the component (A) be preferably 10 to 99 wt. %, more preferably 40 to 99 wt. %, based on the catalyst weight. It is also preferred that an oxide of titanium, silicon, germanium, tin, etc. be used as the oxide of the Group IV element other than zirconium and hafnium, which is mentioned as one of the component (B). Furthermore, when the component (B) is constituted by oxides of Group III and Group V elements, it is preferred that the total content of the oxides of Group III and Group V elements be, calculated as the elements, 0.5 wt. % or more based on the zirconium element weight and the content of amorphous zirconium oxide as the component (A) be 10 to 99 wt. %, based on the catalyst weight. The crystallization temperature of the amorphous zirconium oxide is preferably 450° C. or higher.

It is preferred that the oxide of the Group III element in the catalyst be aluminum oxide, the content thereof be, calculated as the element, 40 to 1 wt. % based on the weight of zirconium element, the oxide of the Group V element in the catalyst be phosphorus oxide, and the content thereof be, calculated as the element, 8 to 0.8 wt. % based on the weight of zirconium element.

BEST MODE FOR CARRYING OUT THE INVENTION

Starting Material Esters

Starting material esters used in the present invention may be any materials containing an ester compound as the main component, and they may be polyesters. It is especially preferred that glyceride esters of saturated or unsaturated aliphatic carboxylic acids (carboxylic acids with the number of carbon atoms of about 8-24) be used. More specifically, it is preferred that triglycerides that are called oils and fats be used. Examples of such oils and fats include vegetable oils and fats such as soybean oils, coconut oil, olive oil, arachis oil, cotton seed oil, sesame oil, palm oil, castor oil, etc., and animal oils and fats such as beef tallow, lard, horse fat, whale oil, sardine oil, mackerel oil, etc. The starting material ester may contain 0 to 30 wt. %, more specifically 1 to 20 wt. % free fatty acid.

Alcohol

Alcohols containing 1 to 3 carbon atoms, in particular, methanol and ethanol, are preferably used as the alcohol employed in accordance with the present invention. Polyhydric alcohols may be also used.

Catalyst

The catalyst used in accordance with the present invention comprises an amorphous zirconium oxide as the main component, and the content of zirconium oxide is 10 to 99 wt. %, preferably 40 to 99 wt. %, even more preferably 80 to 98 wt. %, in case of a catalyst comprising the oxides of a Group III element and/or Group V element as the component (B). Furthermore, the content of zirconium oxide is 10 to 95 wt. %, preferably 40 to 80 wt. %, in the case of a catalyst comprising the oxide of the Group IV element other than zirconium and hafnium, as one of the component (B). Here, zirconium oxide also includes the hydrated oxide state. The term "amorphous" means that substantially no diffraction peaks are observed in X-ray diffraction (XRD). More specifically, the intensity of diffraction peaks is less than the detection limit, or only peaks with an intensity of 2 or less are detected, where the diffraction intensity of crystalline zirconium oxide is taken as 100.

The catalyst employed in accordance with the present invention can contain an oxide of a Group IV element other than zirconium and hafnium as the component (B), and titanium oxide and silicon oxide can be used as this oxide. When titanium oxide is used, the content thereof in the catalyst is 5 to 90 wt. %, preferably 10 to 60 wt. %, and when silicon oxide is used, the content thereof is 1 to 20 wt. %, preferably 2 to 10 wt. %. The total content of the elements of Groups I-II and Groups VI-VII as the catalyst component is 1 wt. % or less, and it is especially preferred that the catalyst substantially not contain these elements, with the content thereof 0.2 wt. % or less. If necessary, a Group VIII element may be added in an amount of 0.1 to 5 parts by weight per 100 parts by weight of the catalyst. In addition, boron oxide, aluminum oxide, yttrium oxide, and lanthanoide element oxides, etc. may be used as a binder.

Further, the oxides of Group III and Group V elements are also effective as the component (B) of the catalyst used in accordance with the present invention. The oxides of those elements are contained at a content of 0.5 wt. % or more, calculated as their elements, based on the zirconium element weight.

Oxides of aluminum, gallium, indium, thallium, and yttrium can be used as the oxide of the Group III element. The content of the oxide of the Group III element is preferably not more than 1/3 of zirconium content, as the weight ratio of the elements. When aluminum oxide is used, the content thereof, is, calculated as the element, 40 to 1 wt. %, preferably 30 to 1 wt. %, even more preferably 25 to 1 wt. %, based on the zirconium element weight.

The Group III element oxide is preferably contained in the catalyst in the state such that it is exposed together with zirconium oxide on the surface of the catalyst and the crystal growth of zirconium oxide is inhibited by the Group III element oxide. As a result, as described hereinbelow, the crystallization temperature of zirconium oxide preferably becomes 450° C. or higher. If the content of the Group III element oxide is too low, the crystal growth of zirconium oxide is enhanced, and if this content is too high, most of the surface of the zirconium oxide is covered with the Group III element oxide, thereby degrading the catalytic activity. The oxide of the Group IV element other than zirconium and hafnium is assumed to act on the zirconium oxide as mentioned about the Group III element oxide.

Oxides of phosphorus, arsenic, antimony, bismuth, etc., can be used as the Group V element oxide. The content thereof is preferably not more than 1/5 of the zirconium element, as an element weight ratio. When phosphorus oxide is used, the content thereof is, calculated as the element, 8 to 0.8 wt. %, in particular, 6 to 1 wt. %, based on the zirconium element weight.

As for the contained Group V element oxide, it is preferred that phosphorus oxide cover the catalyst surface with a monomolecular layer. The catalyst may contain a combination of two or more of the Group III element oxide, the Group IV element oxide and the Group V element oxide. In any case, the crystal growth of zirconium oxide is suppressed, and the crystallization temperature of zirconium oxide is preferably 450° C. or higher, more preferably 500° C. or higher, even more preferably 550° C. or higher. Usually it is 900° C. or less. The crystallization temperature can be measured as a peak temperature of the exothermic peak at which no changes in weight are observed in the thermogravimetric-differential thermal analysis (TG-DTA) conducted by heating from room temperature.

The total content of elements other than the components (A) and (B) mentioned as the catalyst components and Group VIII elements is preferably 1 wt. % or less, more preferably such elements be substantially absent, that is, they are present at 0.2 wt. % or less. Furthermore, if necessary, a Group VIII element may be added in an amount of 0.1 to 5 parts by weight per 100 parts by weight of the catalyst.

In the catalyst employed in accordance with the present invention, the mean particle size is 2 to 200 μm, preferably 4 to 40 μm, the specific surface area is 100 to 400 m$^2$/g, preferably 150 to 400 m$^2$/g, and the central pore diameter D50 is 2 to 10 nm, preferably 2 to 8 nm. The specific surface area and central pore diameter can be measured by a nitrogen adsorption and desorption method. Further, when the catalyst is shaped, alumina having γ, η or other crystallinity may be used as a binder.

Composite oxide powders comprising the components (A) and (B) constituting the catalyst used in accordance with the present invention are generally available and can be purchased, for example, from Daiichi Kigenso Kagaku Kogyo Co., Ltd. Further, composite oxide powders comprising titanium oxide and an oxide of a Group IV element other than titanium, for example, silicon or tin, can be also used as the composite oxide powder to prepare the catalyst for transesterification.

Transesterification

The reaction temperature is such that the starting material ester is in a liquid-phase state and the alcohol is in a vapor-phase state. More specifically, the reaction temperature is 100° C. or higher, preferably 150 to 350° C. No limitation is placed on the reaction pressure. Although the reaction can proceed sufficiently even under an atmospheric pressure of about 0.05 to 0.2 MPa, the reaction pressure is preferably 0.1 to 4 MPa, more preferably 0.1 to 3 MPa. The reaction may be also conducted in the so-called supercritical state. No limitation is placed on the reaction time. However, in a batch mode the reaction time is about 0.1 to 1 hour, and in a flow-through mode the product can be sufficiently obtained at a WHSV (Weight-Hourly Space Velocity) of about 0.5 to 5 (/hour). The ester manufactured by the present reaction is preferably obtained in the form of a liquid phase to facilitate separation from the catalyst. The reaction can be conducted in batch mode or a flow-through mode. The catalyst in accordance with the present invention is preferably used as a fixed bed. In this case, it is not contained in the product and can be separated and recovered.

EXAMPLES

The present invention will be described below in greater detail based on examples thereof.

Example 1

The properties of the composite oxides manufactured by Daiichi Kigenso Kagaku Kogyo Co., Ltd., which were used as the catalysts, are presented in Table 1. A zirconium oxide powder (reagent manufactured by MEL Co., Ltd. (Great Britain)) fired in air for 2 hours at a temperature of 400° C. (Z-1) was used for comparison. The presence of X-ray diffraction peaks was determined by whether or not a diffraction peak exceeding the detection limit was detected at a scanning speed of 4°/min and a scanning width of 0.02° in RAD-1C (CuKα, tube voltage 30 kV, tube current 20 mA) manufactured by Rigaku Denshi Co., Ltd. When there was no peak, exceeding the detection limit or when only a peak of 2 or less was present (the peak intensity of the fired zirconium oxide powder (Z-1) was taken as 100), the peak was assumed to be absent.

Each of those oxides was used as a catalyst, a fixed-bed flow reactor with a length in the up-down direction of 50 cm and an inner diameter of 1 cm was filled with 4 g of the catalyst, soybean oil (manufactured by Kanto Kagaku Co., Ltd.) as a starting material ester and methanol as an alcohol were introduced from the top end, and a conversion rate of the soybean oil in the outlet at the lower end was measured by gas chromatography at a point of time of 4 hours or 20 hours after the test was started.

The reaction conditions were as follows:
reaction pressure: atmospheric pressure,
reaction temperature: 200° C.,
starting material flow rate of soybean oil: 3.0 g/h,
starting material flow rate of methanol: 4.4 g/h, and
WHSV: 1.85/h.

The test results relating to transesterification are shown in Table 1. When the composite oxides of test examples 1 to 6 were used as catalysts, the conversion rate was high. In particular, it is clear that an even higher conversion rate was obtained in test examples 2 to 6 which were the examples using a composite oxide comprising an amorphous zirconium oxide as a catalyst.

TABLE 1

| | Test example | | | | | | |
|---|---|---|---|---|---|---|---|
| | 1 | 2 | 3 | 4 | 5 | 6 | 7 |
| | | | | Oxide number | | | |
| | I-1454 | D-1564 | I-1455 | D-1514 | D-1515 | I-1457 | Z-1 |
| Composition (wt. %) | | | | | | | |
| $ZrO_2$ | 93.08 | 82.10 | 70.22 | 50.02 | 14.12 | 95.73 | 100 |
| $TiO_2$ | 6.92 | 17.90 | 29.78 | 49.98 | 85.88 | 0.0 | 0.0 |
| $SiO_2$ | 0.0 | 0.0 | 0.0 | 0.0 | 0.0 | 4.27 | 0.0 |
| Mean particle size(μm) | 3.9 | 4.0 | 5.82 | 9.21 | 112.7 | 13.1 | — |
| Specific surface area($m^2$/g) | 118.3 | 201.7 | 172.7 | 173.8 | 115.0 | 387.9 | 87 |
| Central pore diameter (nm) | 9.34 | 5.62 | 5.00 | 7.17 | 8.11 | 2.58 | 5.6 |
| X-ray diffraction peak | | | | | | | |
| $ZrO_2$ | Yes | No | No | No | No | No | Yes |
| $TiO_2$ | No | No | Yes | Yes | Yes | No | No |
| $SiO_2$ | No | No | No | No | No | No | No |
| Conversion rate | | | | | | | |
| After 4 hours | 33% | 55% | 51% | 53% | 40% | 54% | 14% |
| After 20 hours | 28% | 48% | 43% | 45% | 36% | 56% | 10% |

Example 2

The properties of the composite oxides manufactured by Daiichi Kigenso Kagaku Kogyo Co., Ltd., which were used as the catalysts, are presented in Table 2. A zirconium oxide powder (reagent manufactured by MEL Co., Ltd. (Great Britain)) fired in air for 2 hours at a temperature of 400° C. (Z-1) was used for comparison. The presence of X-ray diffraction peaks was determined by whether or not a diffraction peak exceeding the detection limit was detected at a scanning speed of 4°/min and a scanning width of 0.02° in RAD-1C (CuKα, tube voltage 30 kV, tube current 20 mA) manufactured by Rigaku Denshi Co., Ltd. When there was no peak exceeding the detection limit or when only a peak of 2 or less was present (the peak intensity of the fired zirconium oxide powder (Z-1) was taken as 100), the peak was assumed to be absent. The thermogravimetric-differential thermal analysis (TG-DTA) for measuring the crystallization temperature was conducted with a device manufactured by Mac-Science Co., Ltd. (TG-DTA2000S) by raising the temperature from room temperature to 1500° C. at a rate of 20° C./min under an air flow.

Each of those oxides were used as a catalyst, a fixed-bed flow reactor with a length in the up-down direction of 50 cm and an inner diameter of 1 cm was filled with 4 g of the catalyst, soybean oil (manufactured by Kanto Kagaku Co., Ltd.) as a starting material ester and methanol as an alcohol were introduced from the top end, and the conversion rate of the soybean oil in the outlet at the lower end was measured by gas chromatography at a point of time of 20 hours after the test was started.

The reaction conditions were as follows:
reaction pressure: atmospheric pressure,
reaction temperature: 200° C. or 250° C.,
starting material flow rate of soybean oil: 3.0 g/h,
starting material flow rate of methanol: 4.4 g/h, and
WHSV: 1.85/h.

The test results relating to transesterification are shown in Table 2. It is clear that a high conversion rate is obtained in Test Examples 8 to 10, which are the examples using a composite oxide comprising an amorphous zirconium oxide as a composite oxide catalyst.

TABLE 2

| | Test examples | | | |
|---|---|---|---|---|
| | 8 | 9 | 10 | 7 |
| Composition | | Oxide number | | |
| (wt. %) | K-1407 | E-1565 | E-1565 | Z-1 |
| $ZrO_2$ | 91.3 | 95.8 | 95.8 | 100 |
| $PO_4$ | 8.7 | 0.0 | 0.0 | 0.0 |
| $Al_2O_3$ | 0.0 | 4.2 | 4.2 | 0.0 |
| Mean particle size (μm) | 22.5 | 4.9 | 4.9 | — |
| Specific surface area ($m^2$/g) | 131 | 197 | 197 | 87 |
| Central pore diameter (nm) | — | — | — | 5.6 |
| X-ray diffraction peak | No | No | No | Yes |
| Crystallization temperature | 745° C. | 626° C. | 626° C. | already crystallized |
| Reaction temperature (° C.) | 250 | 200 | 250 | 200 |
| Conversion rate (After 20 hours) | 83% | 59% | 80% | 10% |

Example 3

The properties of the composite oxides manufactured by Daiichi Kigenso Kagaku Kogyo Co., Ltd., which were used as the catalysts, are presented in Table 3. A zirconium oxide powder (reagent manufactured by MEL Co., Ltd. (Great Britain)) fired in air for 2 hours at a temperature of 400° C. (Z-1) was used for comparison. The presence of X-ray diffraction peaks was determined by whether or not a diffraction peak exceeding the detection limit was detected at a scanning speed of 4°/min and a scanning width of 0.02° in RAD-1C (CuKα, tube voltage 30 kV, tube current 20 mA) manufactured by Rigaku Denshi Co., Ltd. When there was no peak exceeding the detection limit or when only a peak of 2 or less was present (the peak intensity of the fired zirconium oxide powder (Z-1) was taken as 100), the peak was assumed to be absent. The thermogravimetric-differential thermal analysis (TG-DTA) for measuring the crystallization temperature was conducted with a device manufactured by Mac-Science Co., Ltd. (TG-DTA2000S) by raising the temperature from room temperature to 1500° C. at a rate of 20° C./min under an air flow.

Each of those oxides was used as a catalyst, a fixed-bed flow reactor with a length in the up-down direction of 50 cm and an inner diameter of 1 cm was filled with 4 g of the catalyst, soybean oil (manufactured by Kanto Kagaku Co., Ltd.) as a starting material ester and methanol as an alcohol were introduced from the top end, and a conversion rate of the soybean oil in the outlet at the lower end was measured by gas chromatography at a point of time of 20 to 48 hours after the test was started.

The reaction conditions were as follows:
reaction pressure: atmospheric pressure, 1.0 MPa, 2.0 MPa or 3 MPa
reaction temperature: 200° C. to 250° C.,
starting material flow rate of soybean oil: 3.0 g/h,
starting material flow rate of methanol: 4.4 g/h, and
WHSV: 1.85/h.

The test results relating to transesterification are shown in Table 3. It is clear that a high conversion rate is obtained in Test Examples 11 to 23, which are the examples using a composite oxide comprising an amorphous zirconium oxide as a composite oxide catalyst. Among Test Examples 18 to 23, Test Examples 18 and 22 containing a somewhat low or high titanium oxide content showed a slightly low conversion rate as compared with other test samples.

TABLE 3

| | Test example | | | | | | |
|---|---|---|---|---|---|---|---|
| | 11 | 12 | 13 | 14 | 15 | 16 | 17 |
| | | | | Oxide number | | | |
| | E-1565 | E-1565 | K-1570 | K-1570 | K-1570 | K-1570 | K-1570 |
| Composition (wt. %) | | | | | | | |
| $ZrO_2$ | 95.8 | 95.8 | 95.0 | 95.0 | 95.0 | 95.0 | 95.0 |
| $PO_4$ | 0.0 | 0.0 | 0.0 | 0.0 | 0.0 | 0.0 | 0.0 |
| $Al_2O_3$ | 4.2 | 4.2 | 5.0 | 5.0 | 5.0 | 5.0 | 5.0 |
| $TiO_2$ | 0.0 | 0.0 | 0.0 | 0.0 | 0.0 | 0.0 | 0.0 |
| $SiO_2$ | 0.0 | 0.0 | 0.0 | 0.0 | 0.0 | 0.0 | 0.0 |
| Mean particle size (μm) | 4.9 | 4.9 | 160.7 | 160.7 | 160.7 | 160.7 | 160.7 |
| Specific surface area ($m^2$/g) | 197 | 197 | 179 | 179 | 179 | 179 | 179 |
| Central pore diameter (nm) | 3.9 | 3.9 | 4.3 | 4.3 | 4.3 | 4.3 | 4.3 |
| X-ray diffraction peak | | | | | | | |
| $ZrO_2$ | No | No | No | No | No | No | No |
| $PO_4$ | No | No | No | No | No | No | No |
| $Al_2O_3$ | No | No | No | No | No | No | No |
| $TiO_2$ | No | No | No | No | No | No | No |
| $SiO_2$ | No | No | No | No | No | No | No |
| Crystallization temperature(° C.) | 626 | 626 | 642 | 642 | 642 | 642 | 642 |
| Reaction temperature | 200 | 250 | 250 | 250 | 250 | 230 | 210 |
| Reaction Pressure (MPa) | Atmospheric pressure | | 1.0 | 2.0 | 3.0 | 3.0 | 3.0 |
| Conversion rate (%) (reaction time) | 59(20 h) | 80(20 h) | 97(29 h) | 98(25 h) | 98(22 h) | 99(22 h) | 93(46 h) |

| | Test example | | | | | | |
|---|---|---|---|---|---|---|---|
| | 18 | 19 | 20 | 21 | 22 | 23 | 7 |
| | | | | Oxide number | | | |
| | I-1454 | D-1564 | D-1455 | D-1514 | D-1515 | I-1457 | Z-1 |
| Composition (wt. %) | | | | | | | |
| $ZrO_2$ | 93.1 | 82.1 | 70.2 | 50.0 | 14.1 | 95.7 | 100.0 |
| $PO_4$ | 0.0 | 0.0 | 0.0 | 0.0 | 0.0 | 0.0 | 0.0 |
| $Al_2O_3$ | 0.0 | 0.0 | 0.0 | 0.0 | 0.0 | 0.0 | 0.0 |
| $TiO_2$ | 6.9 | 17.9 | 29.8 | 50.0 | 85.9 | 0.0 | 0.0 |
| $SiO_2$ | 0.0 | 0.0 | 0.0 | 0.0 | 0.0 | 4.3 | 0.0 |
| Mean particle size (μm) | 3.9 | 4.0 | 5.8 | 9.2 | 112.7 | 13.1 | — |

TABLE 3-continued

|  |  |  |  |  |  |  |  |
|---|---|---|---|---|---|---|---|
| Specific surface area (m²/g) | 118 | 202 | 173 | 174 | 115 | 388 | 87 |
| Central pore diameter (nm) | 9.3 | 5.6 | 5.0 | 7.2 | 8.1 | 2.6 | 5.6 |
| X-ray diffraction peak |  |  |  |  |  |  |  |
| ZrO₂ | Yes | No | No | No | No | No | Yes |
| PO₄ | No | No | No | No | No | No | No |
| Al₂O₃ | No | No | No | No | No | No | No |
| TiO₂ | No | No | Yes | Yes | Yes | No | No |
| SiO₂ | No | No | No | No | No | No | No |
| Crystallization temperature(° C.) | 759 | 605 | 576 | 600 | 725 | 559 | Already crystallized |
| Reaction temperature | 200 | 200 | 200 | 200 | 200 | 200 | 200 |
| Reaction Pressure (MPa) | Atmospheric pressure | | | | | | |
| Conversion rate (%) (reaction time) | 28(20 h) | 48(20 h) | 43(20 h) | 45(20 h) | 36(20 h) | 56(20 h) | 10(20 h) |

INDUSTRIAL APPLICABILITY

In accordance with the present invention, the transesterification reaction can be conducted within a short time under a pressure of the order of normal pressure. Furthermore, the product and catalyst can be easily separated. Therefore, the target ester can be produced with good efficiency.

The invention claimed is:

1. A method for the manufacture of an ester by transesterification comprising the step of bringing a starting material ester in a liquid phase state and an alcohol in a vapor phase state into contact with an amorphous solid acid catalyst consisting of (A) an amorphous zirconium oxide and (B) aluminum oxide, wherein the content of the aluminum oxide is, calculated as the element, 25 to 1 wt. % based on the zirconium element weight.

2. The method according to claim 1, wherein the starting material ester is an oil or fat and the alcohol is methanol or ethanol.

3. The method according to claim 1, wherein the starting material ester is a glyceride ester of a saturated or unsaturated aliphatic carboxylic acid having from 8-24 carbon atoms.

4. A method for the manufacture of an ester by transesterification comprising the step of bringing a starting material ester in a liquid phase state and an alcohol in a vapor phase state into contact with an amorphous solid acid catalyst consisting of (A) an amorphous zirconium oxide and (B) phosphorus oxide, wherein the content of the phosphorus oxide is, calculated as the element, 6 to 1 wt. % based on the zirconium element weight.

5. The method according to claim 4, wherein the starting material ester is an oil or fat, and the alcohol is methanol or ethanol.

6. The method according to claim 4, wherein the starting material ester is a glyceride ester of a saturated or unsaturated aliphatic carboxylic acid having from 8-24 carbon atoms.

7. A method for the manufacture of an ester by transesterification comprising the step of bringing a starting material ester in a liquid phase state and an alcohol in a vapor phase state into contact with an amorphous solid acid catalyst consisting of (A) an amorphous zirconium oxide and (B) titanium oxide, wherein the content of the amorphous zirconium oxide in the catalyst is 40 to 90 wt. % and the content of the titanium oxide is 60 to 10 wt. % in the catalyst.

8. The method according to claim 7, wherein the starting material ester is an oil or fat, and the alcohol is methanol or ethanol.

9. The method according to claim 7, wherein the starting material ester is a glyceride ester of a saturated or unsaturated aliphatic carboxylic acid having from 8-24 carbon atoms.

* * * * *